(12) United States Patent
Schmucki et al.

(10) Patent No.: US 7,833,224 B2
(45) Date of Patent: Nov. 16, 2010

(54) CLAMPING DEVICE FOR BONE FIXATION ELEMENTS

(75) Inventors: Daniel Schmucki, Stallikon (CH); Patrizio Frigeri, Uster (CH); Peter Messmer, Oberwil (CH)

(73) Assignee: Synthes USA, LLC, West Chester, PA (US)

( * ) Notice: Subject to any disclaimer, the term of this patent is extended or adjusted under 35 U.S.C. 154(b) by 971 days.

(21) Appl. No.: 11/048,233

(22) Filed: Feb. 1, 2005

(65) Prior Publication Data

US 2005/0234471 A1   Oct. 20, 2005

(30) Foreign Application Priority Data

Feb. 2, 2004   (DE)   ................... 20 2004 001 504 U

(51) Int. Cl.
*A61F 5/04*   (2006.01)
(52) U.S. Cl. ........................................................ 606/57
(58) Field of Classification Search .................. 606/57, 606/104, 99, 250
See application file for complete search history.

(56) References Cited

U.S. PATENT DOCUMENTS

| 4,911,154 | A | * | 3/1990 | Vickers | ....................... 606/104 |
|---|---|---|---|---|---|
| 5,281,230 | A | * | 1/1994 | Heidmueller | ................ 606/127 |
| 5,487,744 | A | * | 1/1996 | Howland | ...................... 606/264 |
| 5,649,931 | A | * | 7/1997 | Bryant et al. | ................ 606/104 |
| 5,927,165 | A | * | 7/1999 | Vasudeva | ...................... 81/448 |
| 6,673,078 | B1 | * | 1/2004 | Muncie | ....................... 606/104 |

FOREIGN PATENT DOCUMENTS

| DE | 198 59 135 | 12/1998 |
|---|---|---|
| DE | 100 39 690 | 8/2000 |
| EP | 1 013 233 A2 | 12/1999 |

* cited by examiner

*Primary Examiner*—Eduardo C Robert
*Assistant Examiner*—Elana B Fisher
(74) *Attorney, Agent, or Firm*—Fay Kaplun & Marcin, LLP

(57) ABSTRACT

A device for clamping fixation elements, which have been inserted into bone, for manipulating fragments of a fractured bone. The device incorporating a hollow body with a cavity having a wall, a clamping body moveable within the cavity between a first position and a second position, and a clamping device operably connected to the clamping body for moving the clamping body between the first position and the second position. The device being sized and configured so that when the clamping body is in the first position a free end of the fixation element(s) may be positioned between the clamping body and the wall of the cavity. Once the fixation element(s) is properly positioned within the cavity, the clamping device may be used to move the clamping body into the cavity, thereby wedging the fixation element(s) between the clamping body and the wall of the cavity. A bone fragment may then be manipulated using the device.

15 Claims, 2 Drawing Sheets

CLAMPING DEVICE FOR BONE FIXATION ELEMENTS

CROSS REFERENCE TO RELATED APPLICATION

The present application claims priority to German Utility Model Application No. 20 2004 001 504.8, filed Feb. 2, 2004, the entire content of which is expressly incorporated herein by reference thereto.

FIELD OF THE INVENTION

The present invention relates to a device for manipulating bone and, in particular, a device for clamping bone fixation elements, which are attached to bone, for manipulating fragments of a fractured bone.

BACKGROUND OF THE INVENTION

Bone fractures, especially fractures of the proximal femoral shaft, have proven difficult to manipulate in preparation for internal fixation. For example, when proximal shaft fractures of the femur occur, the distal end of the proximal fragment rotates anterior (flexion) and lateral (abduction) creating difficulty in accessing the piriformis fossa and/or the desired entry point for intramedullary nailing or in performing other methods of internal fixation.

Several devices for aligning fractured bones are described in the prior art. For example, WO 02/096294 discloses a device for aligning bones. The device includes an elongated shaft which connects a handle, located at a proximal end of the device, to a bone grappling claw, located at a distal end of the device. The shaft and handle define a channel which may receive a compression rod. The claw is positioned around the bone and the rod is moved in the channel towards the claw thereby positioning the bone between the rod and the claw. The positioning of the claw around the bone may necessitate the detachment of the soft tissue surrounding the bone.

There remains a need for a device which can be used to manipulate a bone without the need to detach soft tissue surrounding the bone.

SUMMARY OF THE INVENTION

The device of the present invention may include a hollow body defining a cavity, a longitudinal axis, a front end, a rear end, a clamping body which may be moved axially within the cavity, and a clamping device which may be operably associated with the clamping body. The clamping device may be connected to the clamping body by a connecting member (e.g., a rod or bar) and may be used to move the clamping body axially within the cavity and along the longitudinal axis of the hollow body.

A free end of at least one bone fixation element (e.g., Kirschner wires, bone pins, screws) may be inserted into the cavity of the hollow body, the other end of the at least one bone fixation element may be inserted into bone. The cavity may have a wall and may comprise a conical segment and a cylindrical segment. A first end of the conical segment may be positioned proximate the front end of the cavity and a second end of the conical segment may be positioned within the hollow body. The cylindrical segment may be positioned adjacent the second end of the conical segment. The conical segment may taper from the first end to the second end such that a first dimension at the first end of the conical segment may be greater than a second dimension at the second end of the conical segment. The second dimension may be the same as the diameter of the cylindrical segment. In another embodiment, the cavity may comprise only a conical segment.

The clamping device may include a screw connection having a sleeve which may be rotated to move the clamping body axially within the cavity. Additionally, the clamping device may also include a mechanism having a lever for locking the clamping body in a fixed position in the cavity of the hollow body. Using the clamping device, an operator may move the clamping body out of the cavity so that the fixation element(s) may be inserted between an external surface of the clamping body and the wall of the cavity. The clamping device may also be used to move the clamping body into the cavity to wedge the fixation element(s) between the external surface of the clamping body and the wall of the cavity.

In one embodiment, the lever may have a loosened or unlocked position and a tightened or locked position. The sleeve of the screw connection may include external threads which may engage internal threads formed in a borehole in the hollow body. With the lever in the loosened position, the sleeve may be rotated in a first direction, drawing the sleeve into the hollow body thereby causing the clamping body to move out of the cavity of the hollow body so that a free end of a fixation element, which may have another end positioned in a bone fragment, may be inserted into the cavity between the clamping body and the cavity wall. The sleeve may then be rotated in a second direction, drawing the sleeve out of the hollow body and causing the clamping body to move into the cavity of the hollow body. The clamping body may include grooves for receiving the fixation element(s). As the clamping body moves further into the cavity, the fixation element(s) may be wedged between the clamping body and the wall of the cavity. Thereafter, the lever may be moved to the tightened position, thereby locking the clamping body within the cavity and fixing the fixation element(s) with respect to the device of the present invention. An operator may use the device to manipulate the fixation element(s)s and, thus, manipulate bone.

Some advantages achieved by the present invention include:

- only small incisions in the body may be necessary and detachment of the soft tissue surrounding the bones may be unnecessary;
- fixation elements may be attached to the bone such that the fixation elements may not penetrate into the medullary space or pass through the bone and, therefore, a medullary pin may be introduced into the medullary space of the bone without removing the device of the present invention, and
- the fixation elements may be disposed in the bone so that a bone plate may be placed on the surface of the bone without removing the device of the present invention.

BRIEF DESCRIPTION OF THE DRAWINGS

The present invention may be better understood by reference to the following drawings, wherein like reference numerals represent like elements. The drawings are merely exemplary to illustrate certain features that may be used singularly or in combination with other features and the present invention should not be limited to the embodiments shown.

DETAILED DESCRIPTION

Figure 1:
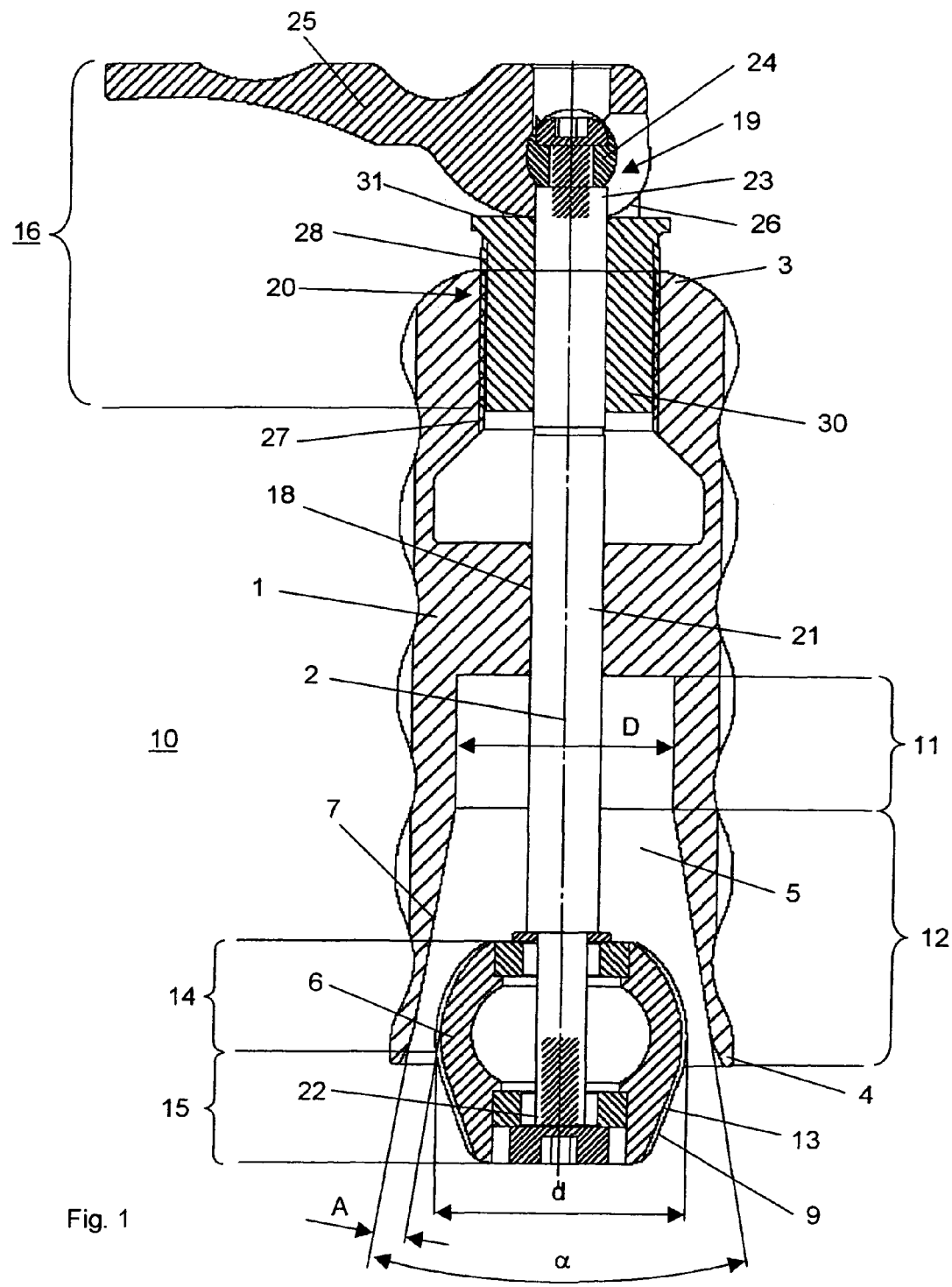
FIG. 1 is a cross-sectional view of an embodiment of the device of the present invention.

As shown in FIG. 1, the device 10 of the present invention includes a hollow body 1 having a longitudinal axis 2, a clamping body 6 which may be moved axially and fixed in a cavity 5 of the hollow body 1, and a clamping device 16 which may be disposed at a rear end 3 of the hollow body 1. It should, however, be understood that those of ordinary skill in the art will recognize many modifications and substitutions which may be made to various elements of the present invention.

Figure 2:
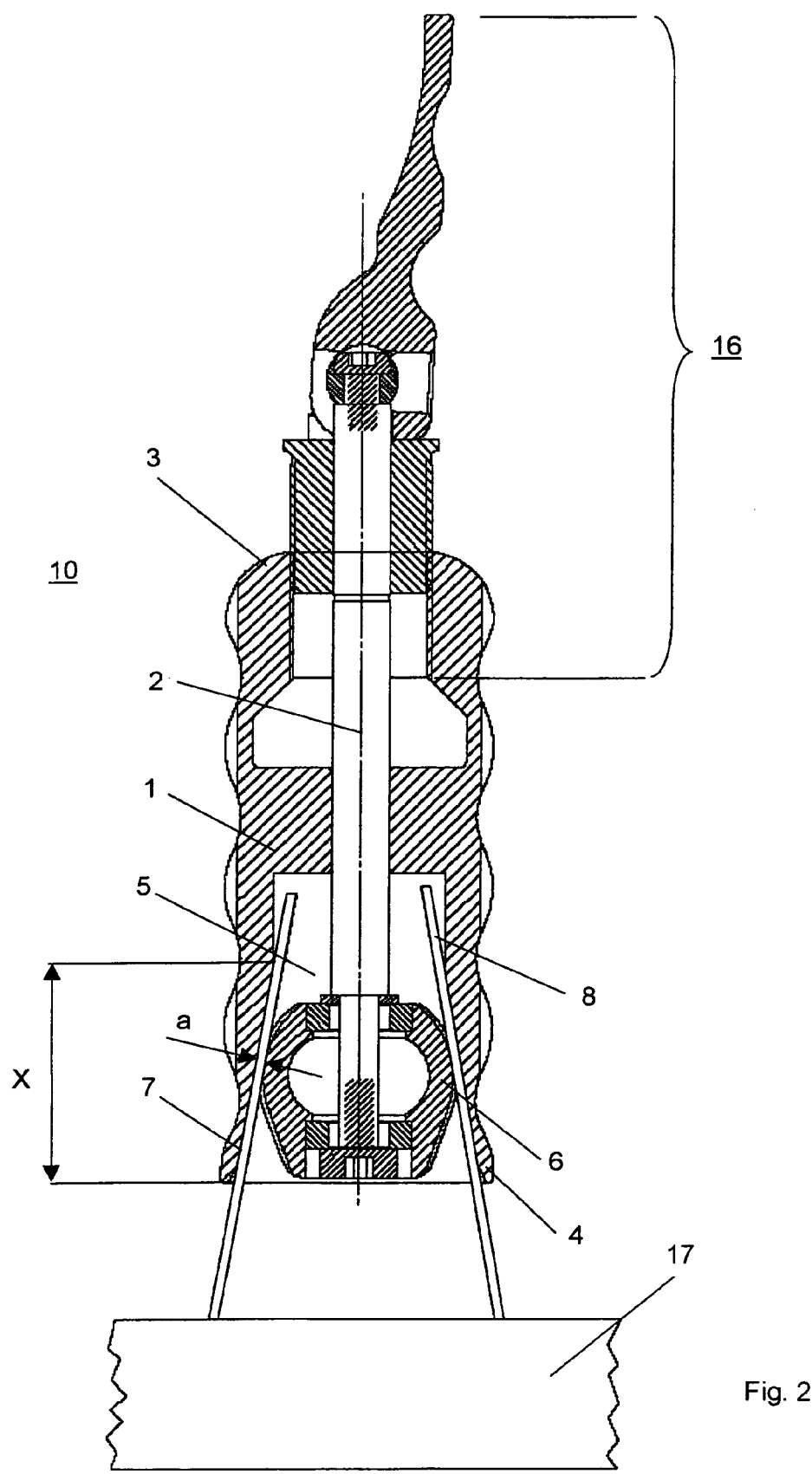
FIG. 2 is another cross-sectional view of an embodiment of the device of the present invention engaging fixation elements inserted into bone.

The clamping body 6 may be moved between a first position, for example, as shown in FIG. 1, and a second position, for example, as shown in FIG. 2. In the first position, there may be a first distance A between the clamping body 6 and the wall 7 of the cavity 5. The first distance A may sized and configured for introducing one or more bone fixation elements (e.g., Kirschner wires 8) into a front end 4 of the hollow body 1, past the clamping body 6 and into the cavity 5 between the clamping body 6 and the wall 7 of the cavity 5. Distance A may be between about 3.0 mm and about 6.0 mm. In the second position, there may be a second distance "a" between the clamping body 6 and the wall 7 of the cavity 5. Preferably, distance "a" is less than distance A so that a fixation element may be wedged between the clamping body 6 and the wall 7 of the cavity 5. Distance "a" may be between about 1.0 mm and about 3.0 mm. In one preferred embodiment, the ratio of distance "a" to distance A (a: A) may be between about 0.1 and about 0.9.

As shown in FIG. 1, the cavity 5 may include two separate segments. For example, the cavity 5 may include a conical segment 12 at the front end 4 of the hollow body 1 and a hollow cylindrical segment 11 which may adjoin the conical segment 12. Alternatively, the cavity 5 may include only a single conical segment 12. It will be appreciated, however, by one skilled in the art that other shapes may be used to form the cavity 5.

The cylindrical segment 11 and the conical segment 12 may have axes which may be coaxial with each other and with the longitudinal axis 2. Moreover, the conical segment 12 may have a first end proximate the front end 4 of the hollow body 1 and a second end located within the hollow body 1 and proximate the cylindrical segment 11. The first end of the conical segment 12 may have a first dimension and the second end of the conical segment 12 may have a second dimension. The conical segment 12 may expand towards the front end 4 of the hollow body 1 such that the first dimension may be greater than the second dimension. The angle $\alpha$ of the conical segment 12 may be between about 5° and about 35° and the wall 7 of the conical segment 12 of the cavity 5 may extend along at least a longitudinal section X of the cavity 5. It will be appreciated by one skilled in the art that the minimum internal diameter D of the conical segment 12 may correspond to the internal diameter of the hollow cylindrical segment 11.

The clamping body 6 may move within the cavity 5 and may have a maximum external diameter d, which may be larger than the minimum internal diameter D of the conical segment 12. The clamping body 6 may be positioned within the hollow body 1 so that the clamping body 6 may be centered in the device 10 and may be used to clamp fixation elements simultaneously. Fixation elements of different sizes may be used with the device 10. For example, Kirschner wires 8 having diameters ranging, for example, from about 1.0 mm to about 3.5 mm, may be used with the device 10.

To clamp Kirshner wires 8 in the device 10, the clamping body 6 may be moved towards the rear end 3 of the hollow body 1 such that the Kirschner wires 8 may be clamped in the gap between the wall 7 of the conical segment 12 and an external surface 9 of the clamping body 6. By moving the clamping body 6 towards the rear end 3 of the hollow body 1, the gap between the wall 7 of the conical segment 12 and the external surface 9 of the clamping body 6 may be decreased. Moreover, the external surface 9 of the clamping body 6 may include grooves 13, which may be distributed uniformly on the periphery of the surface 9 and extend on meridians. Such a configuration may enable fixation elements, such as Kirschner wires 8, to be captured positively in the grooves 13 and guided laterally. In this way, an increased torque may be transferred about the longitudinal axis 2.

To simplify the introduction of the fixation elements into the gap between the wall 7 of the cavity 5 and the external surface 9 of the clamping body 6, the clamping body 6 may be spherically convex in shape on an axial section 14, which may be directed towards the rear end 3 of the hollow body 1, and conical in shape on an axial section 15, which may be directed towards the front end 4 of the hollow body 1. This configuration may produce small contact zone(s) between the fixation elements and the clamping body 6 and may result in larger clamping forces being exerted on the fixation elements.

A clamping device 16 may be used to move the clamping body 6 with respect to the hollow body 1 and to axially fix the clamping body 6 during the clamping of the fixation elements. The clamping device 16 may be connected to a connecting member, for example, rod 21 which, in turn, may be operably attached to the clamping body 6 so that movement of the clamping device 16 may result in corresponding movement of the clamping body 6. The clamping body 6 may be attached to the front end 22 of the rod 21. The rod 21 may be guided in a central borehole 18 passing coaxially through the hollow body 1. The clamping body 6 may be connected with the rod 21 such that the clamping body 6 may be moved axially along the longitudinal axis 2 and may be centered within the cavity 5. This may enable fixation elements of different diameters to be clamped between the clamping body 6 and the wall 7 of the cavity 5.

In one embodiment, the device 10 may incorporate a mechanism 19 or a screw connection 20 to move the clamping body 6 with respect to the hollow body 1. In other embodiments, the device 10 may incorporate both the mechanism 19 and the screw connection 20 to move the clamping body 6 within the cavity 5.

The mechanism 19 may be located at the rear end 23 of the rod 21 and the screw connection 20 may be located at the rear end 3 of the hollow body 1. The mechanism 19 may include a clamping lever 25 with a contact surface 26. The contact surface 26 may be, for example, cylindrical in shape and may be eccentric with respect to an axis of rotation 24. The clamping lever 25 may swivel about the axis of rotation 24, which may be orthogonal to the longitudinal axis 2. For example, the clamping lever 25 may be rotated between a first position, as shown in FIG. 1, and a second position, as shown in FIG. 2. Moreover, the construction of the mechanism 19 may enable an operator to assert a large clamping force on a fixation element. The mechanism 19 may also function as a safeguard preventing the clamping device 16 from loosening unintentionally and, thereby, releasing the fixation elements.

The screw connection 20 may have an axis which may be coaxial with the longitudinal axis 2. Rotating the screw connection 20 may cause the clamping body 6 to move towards the rear end 3 of the hollow body 1 in an axial direction along the longitudinal axis 2. The screw connection 20 may be rotated until the external surface 9 of the clamping body 6 contacts the fixation elements and causes the fixation elements to be pressed against the wall 7 of the cavity 5. Rotating the screw connection 20 in the opposite direction may cause the clamping body 6 to move towards the front end 4 of the hollow body 1.

The axially adjustable screw connection 20 may include a sleeve 30 having an external threaded portion 28 for engaging an internal threaded portion 27 formed in an enlarged portion of the borehole 18 at the rear end 3 of the hollow body 1. The external threaded portion 28 may engage the internal threaded portion 27 such that when the sleeve 30 is rotated in a first direction, the clamping body 6 may move out of the cavity 5 (away from the rear end 3), and when the sleeve is rotated in a second direction, the clamping body 6 may move into the cavity 5 (towards the rear end 3). The rod 21 may pass through the sleeve 30 and may be dimensioned to extend between the clamping body 6 and the clamping lever 25 such that the contact surface 26 of the clamping lever 25 may rest on the outer end surface 31 of the sleeve 30.

In use, a first end of a pair of fixation elements (e.g., Kirschner wires 8) may be inserted (e.g., drilled, hammered, etc.) by a surgeon into a bone 17. Alternatively, as appreciated by one skilled in the art, any number of fixation elements may be inserted into bone 17. In an embodiment wherein the device 10 includes both a mechanism 19 and a screw connection 20, the clamp lever 25 may be rotated into the position shown in FIG. 2 (i.e., the loosened or unlocked position). The clamping body 6 may be moved axially out of the cavity 5 to a certain extent by rotating the sleeve 30 in the first direction until the clamping body 6 is in a first position. In the first position, a second end of the fixation element(s) (i.e., the end of the fixation element(s) which has not been inserted into bone) may be introduced into the gap between the clamping body 6 and the wall 7 of the cavity 5. Thereafter, the sleeve 30 may be rotated in the second direction until the clamping body 6 is moved into the second position so that the external surface 9 of the clamping body 6 contacts the second end of the fixation element(s) and causes the fixation element(s) to be pressed against the wall 7 of the cavity 5. The lever 25 may then be rotated into the position shown in FIG. 1 (i.e., the tightened or locked position) to tension the lever 25 and assert an additional upward force on the clamping body 6, which may move the clamping body 6 further into the cavity 5. In this way, the fixation element(s) may be fixed firmly in the gap between the clamping body 6 and the wall 7 of the cavity 5.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. A device for clamping a bone fixation element comprising:
    a hollow body having a cavity, a longitudinal axis, a front end and a rear end, wherein the cavity includes a length extending from a top of an opening at the front end along the longitudinal axis and has a wall;
    a clamping body having an external surface, the clamping body moveable within the cavity between a first position and a second position wherein, in the first position, the external surface of the clamping body is separated from the wall of the cavity by a first distance selected to permit introduction of a bone fixation element through the opening and along the length between the external surface and the wall and, when in the second position, the external surface is separated from the wall by a second distance smaller than the first distance to fix a bone fixation element therebetween via contact with both the external surface and the wall; and
    a clamping device operably associated with the clamping body so that movement of the clamping device moves the clamping body between the first position and the second position, wherein a shape of the clamping body at the first position is the same as at the second position.

2. The device of claim 1, wherein the cavity comprises a conical segment having a first end, which is proximate the front end of the hollow body and which has a first dimension, and a second end, which is located within the hollow body and which has a second dimension, the first dimension being greater than the second dimension.

3. The device of claim 2, wherein the conical portion has an angle .alpha. which is between about 5° and about 35°.

4. The device of claim 2, wherein the cavity further comprises a cylindrical segment adjoining the second end of the conical segment.

5. The device of claim 1, wherein the clamping device comprises a mechanism having a lever and a sleeve having a threaded portion.

6. The device of claim 5, wherein the hollow body further comprises a borehole having threads for engaging the threaded portion of the sleeve.

7. The device of claim 1, wherein the clamping body has a first axial section directed towards the rear end of the hollow body and a second axial section directed towards the front end of the hollow body, wherein the first axial section is spherically convex in shape and the second axial section is conical in shape.

8. The device of claim 1, wherein the external surface of the clamping body includes grooves for gripping the bone fixation element.

9. The device of claim 8, wherein the grooves extend uniformly on a periphery of the external surface of the clamping body and extend on meridians.

10. The device of claim 1, wherein the first distance is between about 3.0 mm and about 6.0 mm.

11. The device of claim 10, wherein the second distance is between about 1.0 mm and about 3.0 mm.

12. The device of claim 11, wherein the ratio of the second distance to the first distance is between about 0.1 and about 0.9.

13. The device of claim 1, further comprising a rod connecting the clamping device to the clamping body.

14. The device of claim 1, wherein the clamping body and the wall of the cavity are sized and shaped so that, when in the first position, a plurality of bone fixation elements may be received therebetween.

15. The device of claim 1, wherein a bone fixation element is fixed at a location between the external surface and the wall that is laterally displaced from the longitudinal axis.

* * * * *